United States Patent
Mortimer (12)

(10) Patent No.: US 11,027,157 B1
(45) Date of Patent: Jun. 8, 2021

(54) FACE COVERING APPARATUS AND METHOD OF USING THE SAME

(71) Applicant: John S. Mortimer, Frankfort, IL (US)

(72) Inventor: John S. Mortimer, Frankfort, IL (US)

( * ) Notice: Subject to any disclaimer, the term of this patent is extended or adjusted under 35 U.S.C. 154(b) by 93 days.

(21) Appl. No.: 16/884,482

(22) Filed: May 27, 2020

Related U.S. Application Data

(60) Provisional application No. 63/006,813, filed on Apr. 8, 2020.

(51) Int. Cl.
*A62B 23/02* (2006.01)
*A41D 13/11* (2006.01)
*A61F 9/02* (2006.01)
*A62B 9/04* (2006.01)

(52) U.S. Cl.
CPC ........ *A62B 23/025* (2013.01); *A41D 13/1107* (2013.01); *A41D 13/1184* (2013.01); *A61F 9/029* (2013.01); *A62B 9/04* (2013.01)

(58) Field of Classification Search
CPC ............ A41D 13/1107; A41D 13/1184; A41D 13/1138; A41D 13/1145; A41D 13/1161; A61F 9/029; G02C 7/16; G02C 11/00; A62B 23/025; A62B 9/04
See application file for complete search history.

(56) References Cited

U.S. PATENT DOCUMENTS

| | | | | |
|---|---|---|---|---|
| 1,199,529 A | * | 9/1916 | Collman | A41D 13/1107 128/863 |
| 1,279,884 A | * | 9/1918 | La Roche | A41D 13/1184 2/206 |
| 2,197,973 A | * | 4/1940 | Everett | G02C 5/12 2/13 |
| 2,281,181 A | * | 4/1942 | Clarke | A41D 13/1161 128/204.15 |
| 2,447,450 A | * | 8/1948 | Williams | A41D 13/1161 128/206.13 |
| 2,498,668 A | * | 2/1950 | Fitzsimmons | A41D 13/11 128/863 |
| 2,669,717 A | * | 2/1954 | Diggs | G02C 7/10 2/9 |
| 2,870,446 A | * | 1/1959 | Ross | G02C 11/12 2/12 |

(Continued)

*Primary Examiner* — Heather Mangine
(74) *Attorney, Agent, or Firm* — Wood, Phillips, Katz, Clark & Mortimer

(57) ABSTRACT

A face covering apparatus and method of using the apparatus. A frame is configured to be placed in an operative position on a wearer's head and releasably maintained in the operative position by at least one of: a) resting upon one or both of a wearer's ears and b) frictionally engaging a part of the wearer's head. A covering assembly on the frame has a wall structure with: i) a first region configured to conform to the wearer's face region around the wearer's nose; and ii) a second region configured to conform to the wearer's face region around the wearer's mouth. The face covering apparatus is configured so that with the frame in the operative position on the wearer's head and the wall structure in a blocking position on the frame, the first and second regions on the wall structure together reside in the path of airborne particles moving: A) in a forward direction from the wearer's nostrils and/or mouth; and B) in a rearward direction towards the wearer's nostrils and/or mouth.

29 Claims, 8 Drawing Sheets

(56) References Cited

U.S. PATENT DOCUMENTS

| | | | | |
|---|---|---|---|---|
| 3,038,470 | A | * | 6/1962 | Campbell .......... A41D 13/1161 128/206.16 |
| 3,298,031 | A | * | 1/1967 | Morgan ................. A61F 9/029 2/9 |
| 3,333,585 | A | * | 8/1967 | Barghini ............ A41D 13/1146 128/201.13 |
| 3,413,057 | A | * | 11/1968 | Carmichael .............. G02C 9/04 351/47 |
| 3,757,777 | A | * | 9/1973 | Kaufman ............ A41D 13/1146 128/206.19 |
| 3,991,753 | A | * | 11/1976 | Viesca y Viesca ....................... A41D 13/1184 128/201.12 |
| 4,384,577 | A | * | 5/1983 | Huber ................. A41D 13/1146 128/206.19 |
| 4,454,881 | A | * | 6/1984 | Huber ................. A41D 13/1146 128/206.15 |
| 4,600,002 | A | * | 7/1986 | Maryyanek .......... A62B 23/025 128/206.19 |
| 4,796,621 | A | * | 1/1989 | Barle ................. A41D 13/1146 128/206.19 |
| 4,812,031 | A | * | 3/1989 | Evans .................... G02C 5/001 351/46 |
| 4,821,340 | A | * | 4/1989 | Johnson ................. A41D 13/11 128/863 |
| 4,843,643 | A | * | 7/1989 | Parissenti ............... A41D 13/11 2/13 |
| 4,856,509 | A | * | 8/1989 | Lemelson .......... A41D 13/1146 128/206.19 |
| 4,924,526 | A | * | 5/1990 | Parissenti ............ A61F 9/029 2/13 |
| 4,944,039 | A | * | 7/1990 | Dietrich ................. A41D 13/11 2/13 |
| 4,955,394 | A | * | 9/1990 | Dean .................. A41D 13/1146 128/206.23 |
| D323,570 | S | * | 1/1992 | Jacobson ..................... D16/330 |
| 5,372,504 | A | * | 12/1994 | Buechler ................ G02C 5/001 2/13 |
| 5,374,458 | A | * | 12/1994 | Burgio ............... A41D 13/1146 128/206.16 |
| 5,416,923 | A | * | 5/1995 | Peugh .................... A61F 9/029 2/206 |
| 5,424,787 | A | * | 6/1995 | Zegarelli ............ A41D 13/1161 2/429 |
| 5,558,089 | A | * | 9/1996 | Castiglione ........ A41D 13/1146 128/206.24 |
| 5,619,749 | A | * | 4/1997 | Banuchi ................ A41D 13/11 2/13 |
| 5,704,063 | A | * | 1/1998 | Tilden ................ A41D 13/1107 2/9 |
| 5,710,613 | A | * | 1/1998 | Hughes .................... G02C 7/10 351/45 |
| 5,717,992 | A | * | 2/1998 | Tilghman ................ A61F 9/029 2/206 |
| 5,729,321 | A | * | 3/1998 | Wielhouwer ............ G02C 7/10 2/431 |
| 5,956,119 | A | * | 9/1999 | Gibbs .................... G02C 11/00 2/9 |
| 6,102,039 | A | * | 8/2000 | Springett .................. B32B 5/26 128/206.12 |
| 6,116,903 | A | * | 9/2000 | Zegarelli ............ A41D 13/1115 351/111 |
| D615,119 | S | * | 5/2010 | Palmer ........................ D16/309 |
| 7,836,887 | B1 | * | 11/2010 | Kling ................. A41D 13/1161 128/206.16 |
| 8,857,433 | B1 | * | 10/2014 | Kelly ..................... A61B 90/98 128/206.24 |
| D781,503 | S | * | 3/2017 | Rose ............................ D29/108 |
| 9,675,121 | B1 | * | 6/2017 | Everest ..................... G02C 7/16 |
| 2004/0109131 | A1 | * | 6/2004 | Cole ....................... G02C 11/00 351/158 |
| 2004/0211426 | A1 | * | 10/2004 | Lai ..................... A41D 13/1184 128/206.21 |
| 2004/0237962 | A1 | * | 12/2004 | Russell .................. G02C 11/00 128/201.17 |
| 2006/0230485 | A1 | * | 10/2006 | Lee .................... A41D 13/1176 2/15 |
| 2007/0039620 | A1 | * | 2/2007 | Sustello ............. A41D 13/1161 128/206.22 |
| 2007/0252946 | A1 | * | 11/2007 | Welchel ................. G02C 11/00 351/62 |
| 2008/0143953 | A1 | * | 6/2008 | Welchel ............. A41D 13/1184 351/62 |
| 2009/0071483 | A1 | * | 3/2009 | Son ..................... A41D 13/1161 128/206.13 |
| 2009/0126064 | A1 | * | 5/2009 | Reaux ................ A41D 13/1161 2/15 |
| 2010/0126504 | A1 | * | 5/2010 | Johnstone ............... A61F 9/029 128/202.13 |
| 2010/0218774 | A1 | * | 9/2010 | Flaherty ............. A41D 13/1138 128/863 |
| 2010/0229275 | A1 | * | 9/2010 | Wilson ..................... A61F 9/04 2/15 |
| 2011/0061656 | A1 | * | 3/2011 | Matich ................. A62B 23/025 128/206.25 |
| 2011/0297152 | A1 | * | 12/2011 | Duveen ............. A41D 13/1138 128/203.29 |
| 2012/0036608 | A1 | * | 2/2012 | Beliveau ................ A61F 9/029 2/9 |
| 2012/0103339 | A1 | * | 5/2012 | Koehler ................. A62B 18/02 128/206.14 |
| 2012/0125341 | A1 | * | 5/2012 | Gebrewold ........ A41D 13/1146 128/206.12 |
| 2013/0014316 | A1 | * | 1/2013 | Castro ................ A41D 13/1184 2/424 |
| 2014/0216479 | A1 | * | 8/2014 | Jeong ................. A41D 13/1138 128/863 |
| 2014/0259253 | A1 | * | 9/2014 | Jacob ................ A41D 13/1184 2/15 |
| 2015/0185497 | A1 | * | 7/2015 | Ho ........................... G02C 5/02 351/105 |
| 2015/0245675 | A1 | * | 9/2015 | Chinquee ................ A61F 9/029 2/424 |
| 2016/0001101 | A1 | * | 1/2016 | Sabolis .................... A62B 9/02 128/863 |
| 2016/0016021 | A1 | * | 1/2016 | Duffy ................. A41D 13/1115 128/863 |
| 2016/0139430 | A1 | * | 5/2016 | Rigas .................... G02C 5/001 2/12 |
| 2016/0213959 | A1 | * | 7/2016 | Barklow ............ A41D 13/1107 |
| 2016/0345643 | A1 | * | 12/2016 | Johnson ............. A41D 13/1184 |
| 2017/0251748 | A1 | * | 9/2017 | Imppola ................... A42B 5/00 |
| 2018/0021608 | A1 | * | 1/2018 | Zhou ................... A41D 13/113 128/863 |
| 2018/0104085 | A1 | * | 4/2018 | Castillo ..................... A61F 5/08 |
| 2018/0264161 | A1 | * | 9/2018 | Welch ...................... A61M 16/06 |
| 2018/0353781 | A1 | * | 12/2018 | Liu ........................ A41D 31/125 |
| 2019/0053948 | A1 | * | 2/2019 | Schempp ............. A41D 15/002 |
| 2019/0076680 | A1 | * | 3/2019 | Liu ............................ A62B 9/04 |
| 2019/0143153 | A1 | * | 5/2019 | Lee .......................... A62B 7/10 128/206.12 |
| 2019/0275454 | A1 | * | 9/2019 | Wendland .......... B01D 39/1607 |
| 2020/0100657 | A1 | * | 4/2020 | Lee ......................... A61B 1/233 |
| 2020/0154800 | A1 | * | 5/2020 | Hexsel .................... A62B 18/02 |
| 2020/0192119 | A1 | * | 6/2020 | Chou ....................... A61F 9/029 |

\* cited by examiner

FACE COVERING APPARATUS AND METHOD OF USING THE SAME

CROSS-REFERENCE TO RELATED APPLICATIONS

This is a non-provisional application claiming priority to U.S. Provisional Application No. 63/006,813, filed Apr. 8, 2020, which is incorporated herein by reference.

BACKGROUND OF THE INVENTION

Field of the Invention

This invention relates to wearable devices and, more particularly, to a covering apparatus that can be worn on a user's head to control transmission of particles, via nostrils and/or mouth, to and from the wearer.

Background Art

The coronavirus pandemic has effectively changed how future generations will behave and interact.

Heretofore, in the United States, surgical masks have been worn primarily by medical professionals in environments where avoidance of germ transmission is critical, such as during medical procedures and around individuals with conditions that make them highly vulnerable to contracting diseases or aggravating conditions. The same considerations have prompted a limited use of surgical-type masks by persons at high risk of contracting illness or in environments where a larger population sensitive to germs is present.

Surgical-type masks, or more sophisticated respiratory masks with filters, are also commonly worn in work environments where there is risk of inhalation of fumes, dust, and other particles that could lead to serious illness or other medical conditions.

In some countries, even outside air quality is such that surgical-type masks are a staple to at least limit particle inhalation that after extended periods could lead to respiratory problems or other dangerous health conditions.

However, most persons worldwide choose to travel freely and intermingle, commonly in close proximity to others, throughout daily work and recreational routines, without wearing any type of face covering. Aside from ignoring the consequences of inhaling germ-laden particles, individuals with an illness and in a contagious state, in settings where they are likely to transmit disease, generally do not utilize any type of face covering to avoid oral transmission of germs to surfaces or to other persons.

Generally, persons in most developed countries wearing surgical-type masks in public are viewed with a somewhat critical eye by a large portion of the population. Entering another person's surroundings with a surgical mask conveys the impression that the space is viewed as unsanitary or unsafe, which may be offensive to a hosting person or group.

Another reason that surgical-type masks are not worn regularly in public is that they are generally viewed as unfashionable. Most publicly available masks are bland in appearance and generally stand out against the rest of a person's garb. This problem is aggravated by the fact that the surgical-type masks are commonly held in place by thin elastic bands which cross the wearer's face and exert a pressure thereon that results in potentially long-lasting discolored impressions that stand out when the masks are removed. The tightened bands are also commonly wrapped against the wearer's ears, which is also inherently uncomfortable.

The conventional-type surgical mask also is not practically worn by persons in formal settings where makeup and jewelry are displayed. Further, voluminous hair makes it difficult to attach conventional masks, which also tend to undesirably alter the appearance of carefully coiffed hair.

While public scrutiny is not a problem with wearing surgical-type masks in the privacy of a home, most persons refrain from using such masks primarily due to the discomfort associated with the elastic mounting and the inconvenience of placing the masks on and removing the same—typically an exercise, often awkward, involving use of one, and more commonly both, of a wearer's hands. Whereas common sense would dictate that persons, cognizant of being contagious with transmittable illnesses, should cover their nose and mouths when in the vicinity of other persons in a shared space in their homes and when at risk of transferring germs to surfaces, such as during cooking, the inconvenience associated with such masks has severely limited their practical use.

The response to the coronavirus outbreak and the threat of encountering a future mutation has caused the entire world to take unprecedented precautionary steps throughout their every day to avoid germ transmission to and from surfaces and to and from other individuals who they are required to be in proximity with. While "social distancing" has addressed this problem to a certain degree, close human interaction is impossible to avoid. For example, work stations may be situated so that persons are sharing space in a confronting relationship closer than the currently recommended six foot minimal range. Seating in convention centers, restaurants, stadiums, airplanes, trains, buses, etc. is designed to compactly place individuals in spaces, which creates a constant risk of dangerous germ transmission.

As a practical matter, there currently is no way to motivate an entire group of closely situated individuals at, for example, sporting events, to each don some sort of protective headwear to minimize germ transmission. As noted, the primary barriers to such preventive measures are the generally unsightly nature of surgical-type masks, the inconvenience of putting the same on and taking the same off, and the discomfort associated with wearing conventionally designed surgical-type masks including uncomfortable elastic retention components.

At this point, there is no clear solution to the above problems, as a result of which it is inevitable that the precautionary steps taken to control a pandemic, once there is perception of an "all clear" state, will be abandoned by many in favor of comfort and convenience. As a result, the birth of another virus or the generation and transmission of a mutation of an existing virus is inevitable, with potentially future worldwide disruption of business and widespread health problems.

SUMMARY OF THE INVENTION

In one form, the invention is directed to a face covering apparatus. The face covering apparatus has a frame configured to be placed in an operative position on a wearer's head and releasably maintained in the operative position by at least one of: a) resting upon one or both of the wearer's ears; and b) frictionally engaging a part of the wearer's head. A covering assembly on the frame has a wall structure with: i) a first region configured to conform to the wearer's face region around the wearer's nose; and ii) a second region configured to conform to the wearer's face region around the wearer's mouth. The face covering apparatus is configured so that with the frame in the operative position on the wearer's head and the wall structure in a blocking position on the frame, the first and second regions on the wall structure together reside in the path of airborne particles moving: A) in a forward direction from the wearer's nostrils and/or mouth; and B) in a rearward direction towards the wearer's nostrils and/or mouth.

In one form, the frame is configured to be moved from a position fully spaced from a wearer's head into the operative position by being translated relative to the wearer's head.

In one form, the frame is configured to be translated along a front to rear/rear to front line between the position fully spaced from a wearer's head into the operative position.

In one form, the wall structure has a pre-formed cup shape in which the first and second regions conform at least nominally to the part of a wearer's nose and the face region around the wearer's lips.

In one form, with the frame in the operative position, the first region fully blocks a wearer's nostrils and the second region fully blocks the wearer's mouth as viewed from in front of the wearer.

In one form, the wall structure is at least partially shape retentive and capable of being re-shaped to more closely conform to a wearer's face and be releasably maintained in a re-shaped configuration.

In one form, the wall structure is at all times fixedly maintained in the blocking position on the frame.

In one form, the wall structure is movable relative to the frame between the blocking position and a staging position. With the frame in the operative position, at least a part of the wall structure is moved further away from a wearer's face than with the frame in the staging position and the wall structure in the blocking position.

In one form, at least a part of the wall structure is pivotable relative to the frame to change the wall structure between the operative and staging positions.

In one form, the face covering apparatus further includes at least one lens on the frame that is placed in front of a wearer's eyes with the frame in the operative position.

In one form, the wall structure is configured so that a wearer can inhale and exhale air through the wall structure.

In one form, the wall structure is made from a material through which a wearer can inhale and exhale air and that will trap airborne particles.

In one form, the second region has a width slightly greater than the width of a wearer's lip region.

In one form, the material is a flexible fabric.

In one form, the covering apparatus has a subframe that maintains a shape of the flexible fabric.

In one form, the subframe is selectively reconfigurable to thereby allow the flexible fabric to be conformed at at least one of the first and second regions to a wearer's frontal face region.

In one form, the frame has first and second legs that straddle a part of a wearer's head with the frame in the operative position.

In one form, the covering assembly is cantilever mounted on the frame.

In one form, the covering assembly is mounted in depending fashion relative to a part of the frame.

In one form, the invention is directed to a method of equipping attendees at an event to reduce oral transmission of particles. The method includes the steps of: obtaining a supply of face covering apparatus as described above wherein the wall structure has a forwardly facing surface and wherein information pertaining to the event is visibly present; and distributing the face covering apparatus to attendees of the event to be worn during the event.

In one form, the event is a sporting event. The information relates to the sporting event.

In one form, the information includes a logo associated with a team participating in the event.

In one form, the information is in the form of an advertisement of a product or service.

In one form, the product or service is of a nature independent of the event.

In one form, the step of distributing the face covering apparatus involves selling the face covering apparatus as souvenirs at the event.

In one form, the face covering apparatus further includes at least one lens on the frame that is placed in front of a wearer's eyes with the frame in the operative position.

In one form, the at least one lens is a prescription lens.

In one form, the at least one lens is tinted to block a wearer's eyes from light glare.

In one form, the invention is directed to a method of covering a wearer's face. The method includes the steps of: obtaining the face covering apparatus described above; and placing the frame in the operative position and thereby causing a part of the wall structure to bear against the wearer's face.

In one form, the step of placing the frame in the operative position involves causing a part of the wall structure to conform to the wearer's face.

DETAILED DESCRIPTION OF THE PREFERRED EMBODIMENT

Figure 1:
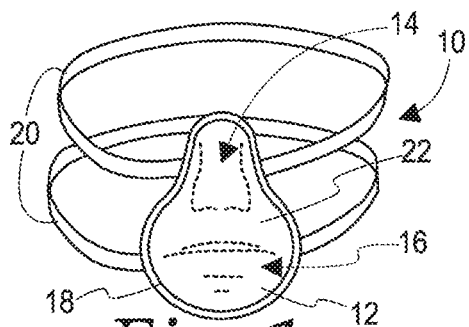
FIG. 1 is a perspective view of a conventional surgical-type mask shown in relationship to a wearer's nose and mouth.
Figure 2:
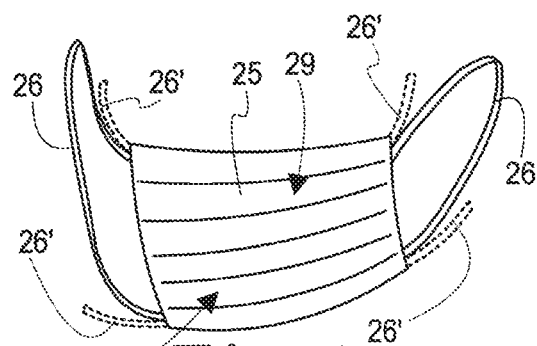
FIG. 2 is a view as in FIG. 1 of an alternative form of conventional surgical-type mask.

FIGS. 1 and 2 depict currently existing surgical-type masks of the general type to which the present invention is directed. In FIG. 1, a mask 10 has a cup-shaped body 12 which tapers upwardly and nominally conforms to a wearer's nose 14 and a wearer's face region around the mouth 16, as viewed from a front perspective. A perimeter edge 18, shown optionally outturned, will rest generally conformingly against the front region of a wearer's face with the mask being worn.

The body 12 is maintained on a wearer's head by elastic straps 20 which, in conjunction with the body 12, encircle a wearer's head, and biasably draw the body 12 rearwardly against the wearer's front facial region.

The body 18 has a continuous wall 22 made from one or more layers that allow air transmission therethrough while having certain filtering capabilities. While different materials are used for such walls, the fabrics commonly used have the ability to block passage of particles of certain size, including, for example, moisture droplets exhaled by the wearer. Other materials are used for purposes of solid particle control, vapor control, etc. Alternatively, only discrete regions may be provided that allow the passage of air to and from a volume bounded cooperatively by the wall 22 and the wearer's face.

The wall 22 is generally made with an upper width slightly greater than that of the wearer's nose and a lower width extending slightly beyond the opposite sides of the wearer's mouth. This allows a compact construction that is not onerous to the wearer yet may provide adequate protection in terms of preventing inhalation and exhalation of the targeted particle size and type.

The existing walls have different degrees of softness and abilities to maintain shape. They generally are pre-formed to define at least a shallow cup shape which might be reshaped upon being worn. Some are impressed with different shapes to increase stiffness, others use more rigid materials, while others use reinforcing elements.

The other prior art mask depicted in FIG. 2 at 24 consists of a generally flat, flexible body 25 with potentially overlapping, typically cloth, layers or a pleated construction which is placed against the mouth and the nose region of a user and drawn conformingly thereagainst by elastic straps 26, one at each side, which wrap around, and are drawn against, a wearer's ears.

Alternatively, vertically spaced strap lengths 26' are provided at each side, with the matching strap lengths 26' at opposite sides tied together and tightened to effect conforming of the body 25 to a wearer's face.

In another alternative form, the straps 26 may be arranged to wrap around a wearer's head as with the mask 10.

With the mask 24, the body 25 is of generally square or rectangular shape, in the latter case normally with the longer dimension arranged horizontally. The body 25 may be made from a single layer of material or using overlapped strips. In one form, the body 25 is made from one material that creates a receptacle 29 within which a potentially different type of material/layer with desired filtering characteristics is replaceably inserted.

As noted above, the masks of the type shown in FIGS. 1 and 2 generally rely upon an elastic biasing force, braced against a part of a wearer's head, to urge the bodies 12, 25 against a wearer's frontal facial region to at least a certain extent seal their perimeter regions to thereby limit the amount of particles that can be transmitted to and from a wearer's nose and mouth without encountering the filtering material making up the bodies 12, 25.

Given the small footprint of each of the depicted bodies 12, 25, the straps 20, 26, 26' in a tightened state are generally directly in contact with the wearer's skin, which can be irritating and which tends to create at least temporary depressions which may become unsightly and irritating until the wearer's tissue relaxes after the masks 10, 24 are removed. The straps 20, 26, 26' under tension may also be uncomfortable around the full circumference of a wearer's head. However, this problem persists so long as a fully surrounding, tightened arrangement is required for the masks 10, 24.

Figure 3:
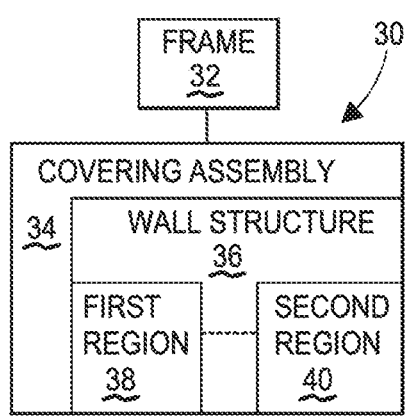
FIG. 3 is a schematic representation of a face covering apparatus, according to the invention, and consisting of a frame and a covering assembly with an associated wall structure.

In FIG. 3, a face covering apparatus, according to the present invention, is shown schematically at 30. The face covering apparatus 30 consists of a frame 32 configured to be placed in an operative position on a wearer's head and releasably maintained in the operative position by at least one of: a) resting upon one or both of a wearer's ears and b) frictionally engaging a part of the wearer's head.

The face covering apparatus 30 further includes a covering assembly 34 on the frame and having a wall structure 36 with: a) a first region 38 configured to conform to at least a part of a wearer's nose; and b) a second region 40 configured to conform to a wearer's face region around a wearer's mouth. The wall structure 36 may be continuous construction defining the first region 38 and second region 40, as indicated by the dotted lines, or such regions 38, 40 may be separate, coordinated parts as described below with respect to FIG. 15.

The face covering apparatus 30 is configured so that with the frame 32 in the operative position on a wearer's head and the wall structure in a blocking position on the frame, the first and second regions 38, 40 on the wall structure 36 together reside in the path of airborne particles moving: a) in a forward direction from a user's nostrils and/or mouth; and b) in a rearward direction towards a user's nostrils and/or mouth.

In various embodiments described herein, the wall structure 36 corresponds in shape to the prior art wall 22. This shape is not to be viewed as limiting as the perimeter shape, width, length, curvature, degree of forward projection, etc. might be changed. For example, the bottom of the wall structure 36 may extend up to the chin, around the chin, or terminate above the chin. The fore-and-aft depth may be selected to create a desired air volume between the front face region and the wall structure 36. Generally, the top region of the wall structure is desirably adjacent the bridge of the wearer's nose with the apparatus being worn. A compact design results with the perimeter of the wall/structure conformed relatively closely around a wearer's nose and mouth, particularly as seen from a front perspective. However, this shape and dimension is not required.

In one form, the frame 32 is configured to be moved from a position fully spaced from the wearer's head into the operative position by simply being translated relative to the wearer's head.

Figure 4:
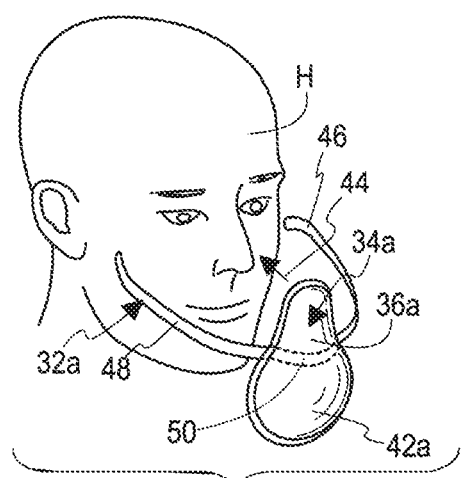
FIG. 4 is a perspective view of one form of face covering apparatus as shown in FIG. 3.

In one form, as shown in FIG. 4, the frame 32a defines, in conjunction with a body 42a on the covering assembly 34a, a "U" shape which can be aligned so that the plane of the U is horizontal and aligned in front of the wearer's head H as depicted in FIG. 4. By being translated horizontally from the spaced position in FIG. 4 in the direction of the arrow 44, legs 46, 48 engage and cooperatively squeeze the sides of the wearer's head to frictionally maintain the frame in its operative position, generally as do conventional headbands. As this occurs, the cup-shaped body 42a, which has generally the configuration of the body 12 on the prior art mask 10 and defines the wall structure 36a, is situated conformingly at the frontal region of the wearer's face over the nose and mouth, to thereby be in a blocking position in front thereof. The body 42a can have sufficient rigidity so that the body 42a, in conjunction with the legs 46, 48 defines the frame 32a. Alternatively, a reinforcing member 50 may be associated with the body to connect to the legs 46, 48 to define the frame 32a.

With this construction, the wearer is offered the convenience of effectively simply press fitting the wall structure 36a into the blocking position, which can be conveniently performed using a single hand. One or both of the legs 46, 48 may be stabilized by bearing on one or both of the wearer's ears.

At the same time, the frame 32a may be comfortably maintained in the operative position, wherein it positively supports the wall structure 36a in the operative position, potentially without any significant discomfort to the user. The depicted arrangement in FIG. 4 is similar to a frame on a pair of eyeglasses, which may be positively held in place without significant uncomfortable pressure on any part of a wearer's head. The engaging location for the legs 46, 48 may be above or below the ears and in the former case may, or may not, rest against the ears for support, stability, and/or fixation.

Figure 5:
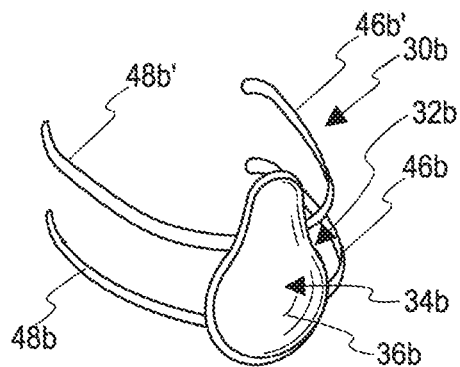
FIG. 5 is a view as in FIG. 4 of another form of face covering apparatus as shown in FIG. 3.

In FIG. 5, a modified form of the inventive face covering apparatus is shown at 30b and incorporates a leg pair 46b, 48b corresponding to the legs 46, 48 in the embodiment in FIG. 4, and an additional pair of legs 46b', 48b' creating a separate "U" closer to the nose location than the legs 46b, 48b, which are vertically in the vicinity of the mouth, whereby the wall structure 36b is stabilized at both regions. The additional legs 46b', 48b' add overall stability to the mounting of the covering assembly 34b without requiring greater force application to the wearer's head to maintain the frame 32b, made up of at least the legs 46b, 48b, 46b', 48b', in the operative position corresponding to that for the frame 32a in FIG. 4.

Figure 6:
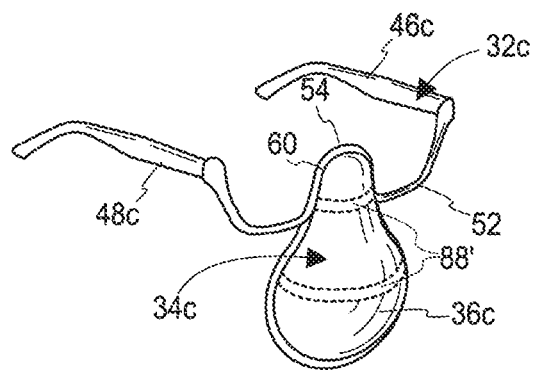
FIG. 6 is a view as in FIGS. 4 and 5 of another form of face covering apparatus as shown in FIG. 3.
Figure 7:
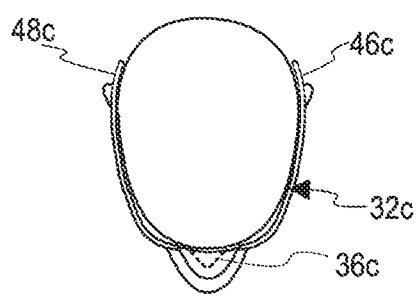
FIG. 7 is a plan view of the face covering apparatus in FIG. 6 with the frame thereon operatively positioned on a wearer's head.

In FIGS. 6 and 7, a further modified form of frame 32c is depicted having similarities to the frames 32a, 32b, however with the frame 32c shaped as a conventional eyeglass frame with legs 46c, 48c and a spanning frame portion 52 with a bridge part 54 that can be supported at a wearer's temple region as is typical of eyeglass frames.

In this embodiment, the wall structure 36c is connected to the frame portion 52, as at the part 54, in a depending fashion. Thus, with the frame 32c moved from a position fully spaced from a wearer's head into an operative position by front to rear translation, the wall structure 36c will be drawn into the blocking position around the wearer's nose and mouth region. The part 54 may be in front of the wall structure portion thereat so that the wall structure 36c is drawn captively against the wearer's face.

The connection between the frame 32c and wall structure 36c can be accomplished in a number of different manners. For example, as shown generally in FIG. 8, each covering assembly 34 may have a subframe 56 joined to the frame 32 using one or more connectors 57 on the frame 32 cooperating with one or more connectors 58 on the subframe 56.

As shown in FIG. 6, as an alternative to discrete type connectors, a part 60 of the wall structure 36c can be integrally formed with the frame 32c.

Figure 9:
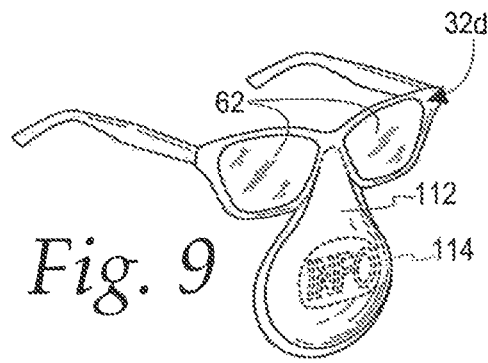
FIG. 9 is a view as in FIG. 6 of another form of face covering apparatus as shown in FIG. 3.

In FIG. 9, a modified form of frame 32d is shown, generally corresponding to the frame 32c, with the exception that the frame 32d has mounted lenses 62, which are situated in front of a wearer's eyes with the frame 32d in an operative position, corresponding to that shown for the frame 32c in FIG. 7. The lenses 62 may be made from a clear material without prescription, with a tinted surface to function as sunglasses, with a decorative see-through surface, or with a particular prescription, such as for reading or to correct for nearsightedness.

There is no limitation as to the connection between the frame 32 and wall structure 36 in the various embodiments. The connection may be permanent or one that is releasable, such as wherein the connectors 57, 58 in FIG. 8 allow for a snap fit, press fit, etc.

Figure 8:
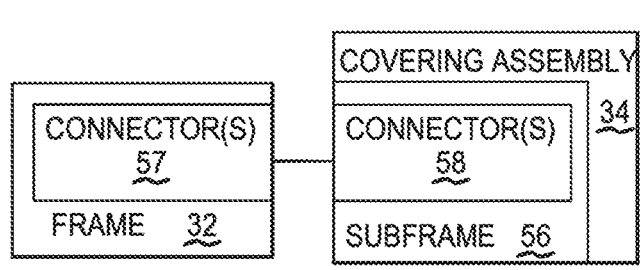
FIG. 8 is a schematic representation of a connection between the frame on the face covering apparatus in FIG. 3 and a subframe associated with the covering assembly.

The ability to connect and disconnect the covering assembly 34 as in FIG. 8 affords interchangeability of covering assemblies 34 and selection of covering assemblies 34 with different appearances, filtering capabilities, etc. Replacement of covering assemblies 34 past usable life is also facilitated.

Figure 10:
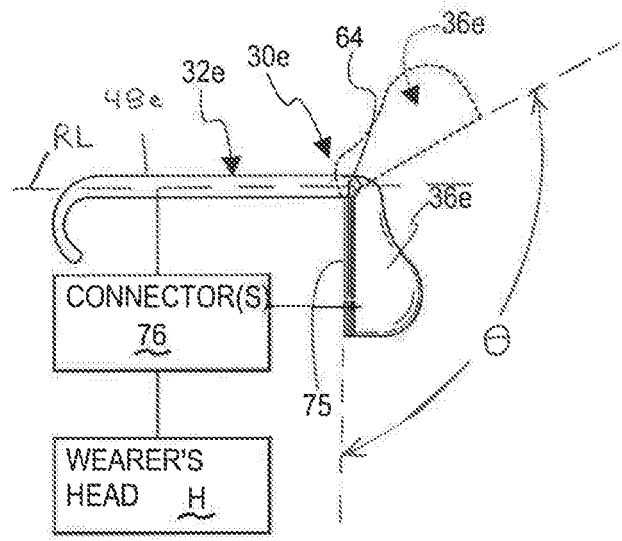
FIG. 10 is a side elevation view of another form of face covering apparatus as shown in FIG. 3 with the wall structure thereon in two different positions.

In FIG. 10, a further modified form of face covering apparatus is shown at 30e and consists of a frame 32e, as in the form of one of those described above or below, and incorporating a wall structure 36e that is repositionable relative to the frame 32e. The frame 32e has elongate legs 48e (one shown) with lengths extending in front-to-rear lines RL on opposite sides of the wearer's head. Accordingly, with the frame 32e in an operative position on a wearer's head, the wearer has the option of maintaining the wall structure 36e in the blocking position, as shown in solid lines, or moving the same to a staging position, one of which is shown in dotted lines in FIG. 10, as might facilitate consumption of food or a beverage. With the frame 32e in the operative position and the wall structure 36e in the staging position, part of the wall structure 36e is located above the lines RL. In this embodiment, the wall structure 36e is pivotable around an axis 64 relative to the frame 32e through an angle θ that is greater than 90°, as viewed from a side perspective. This may be accomplished by a fixed pivot axis as by using one or more pins, using a live hinge arrangement, or by other structure which may not be precisely characterized as a hinge but which allows a similar type movement.

Figure 11:
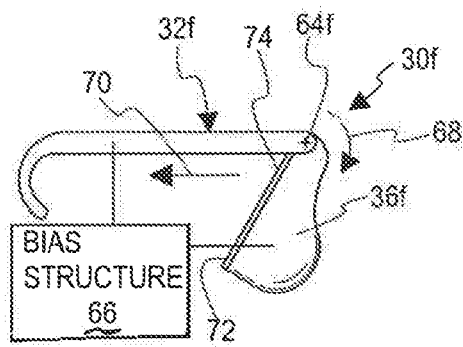
FIG. 11 is a view as in FIG. 10 of another form of face covering apparatus as shown in FIG. 3.

In FIG. 11, a modified form of face covering assembly is shown at 30f with a similar construction as the face covering assembly 30e, with the exception that a biasing structure 66 cooperates between the wall structure 36f and a frame 32f that generates a force tending to pivot the wall structure 36 around an axis 64f in the direction of the arrow 68.

Thus, as the face covering apparatus 30 is advanced from a fully separated position in the direction of the arrow 70 into its operative position, a wearer's face will contact the lower region of the wall structure 36f and progressively load the bias structure 66 so that a residual force urges the wall structure 36f in the pivot direction indicated by the arrow 68. In other words, the restoring force will urge the rear edge 72 of the wall structure 36f against the wearer's face to effect a more positive conformity and/or seal.

To provide better sealing between the wall structure 36f and the wearer's face, a flexible sealing component 74 may be applied at the edge 72 to be compressed between the edge 72 and the wearer's face. Alternatively, the edge material may itself be soft and conformable.

Still further, as shown in FIG. 10, accordion folds 75 may be incorporated to readily conform to different contours of the wearer's face.

In all embodiments the wall structure 36 may have an outturned edge that engages a wearer's face, or may be made without such an outturned edge.

In an alternative manner of enhancing this sealing effect, as shown in FIG. 10, one or more connectors 76 may be utilized to draw the wall structure 36e directly toward the wearer's head or indirectly through the frame 32e. The connector(s) 76 may have an elastic construction or may be otherwise constructed.

Figure 12:
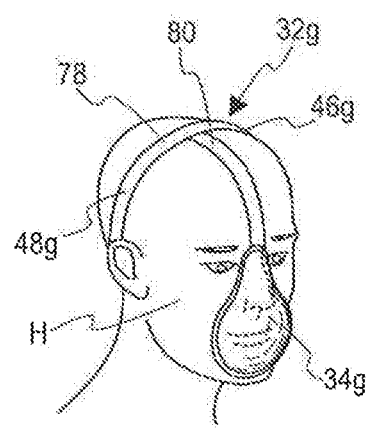
FIG. 12 is a perspective view of another form of face covering apparatus as shown in FIG. 3 with the frame operatively positioned on a wearer's head.

A further alternative frame construction is shown at FIG. 32g in FIG. 12. The frame has a U-shaped body 78 which is placed grippingly over a wearer's head H as a conventional headband by pressing the same from a fully separated position downwardly to cause legs 46g, 48g to straddle, and frictionally grip, the wearer's head. The body 78 has a support 80 which projects forwardly from the body 78. A covering assembly 34g is connected to the support 80 at a location forwardly from the body 78. The connection may be fixed, pivoted, etc.

Figure 13:
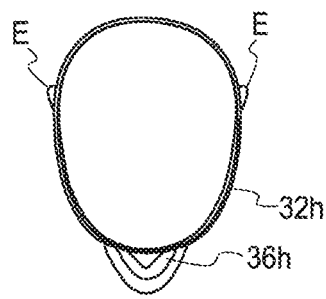
FIG. 13 is a view as in FIG. 7 with another form of the face covering apparatus in FIG. 3.

In FIG. 13, a frame 32h is shown with an associated wall structure 36h, and defines a substantially or fully continuous loop shape which can be directed downwardly over a wearer's head to frictionally grip the same to maintain the operative position therefor. Maintenance of the operative position may be assisted by bearing the frame 32h against one or both of the wearer's ears E.

Figure 14:
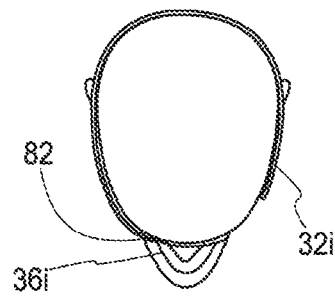
FIG. 14 is a view as in FIG. 13 with still another form of face covering apparatus as shown in FIG. 3.

In FIG. 14, a further modified form of frame 32i is shown wherein the frame 32i does not extend fully around the wearer's head so that a wall structure 36i is cantilever mounted adjacent an end 82 of the frame 32i. This configuration corresponds to another known manner of mounting eyeglasses, wherein the frame wraps around the back of a wearer's head and embraces the sides of the wearer's head to be maintained in place.

It should be understood that the various frame configurations described hereinabove are representative in nature only. The schematic depiction of the face covering apparatus 30 encompasses each of such versions and variations of each of the components therein and their interactions.

Figure 15:
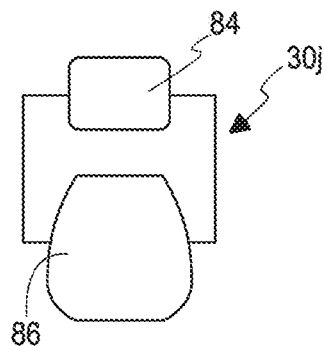
FIG. 15 is a schematic representation of a modified form of wall structure as shown in FIG. 3.

Some additional aspects of different embodiments will now be described. For example, as shown in FIG. 15, while the configuration of the wall structures 36 described has been described above to be generally the same as the wall structure in the prior art mask 10, this is not a requirement. This same general shape is desired because of its effective coverage while being compact in nature. In FIG. 15, the face covering apparatus 30j consists of separate wall parts 84, 86 which cooperative perform the function of the aforementioned wall structure 36. The wall portions 84, 86 may be connected to each other or independently connected to any of the contemplated frame constructions. The wall portion 84 defines the corresponding region 38 for the nose region, whereas the wall portion 86 defines the corresponding second region 40 for the mouth region, as indicated in the schematic showing in FIG. 3.

Figure 16:
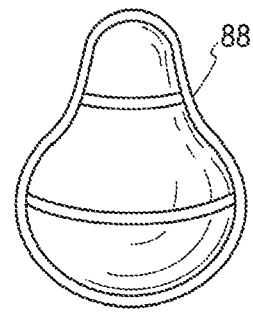
FIG. 16 is a perspective view of a subframe making up part of a wall structure as shown in FIG. 3.
Figure 17:
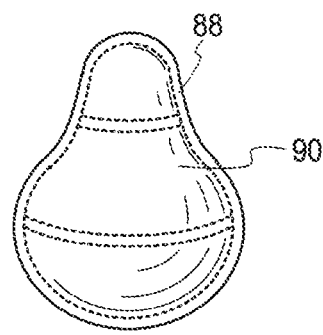
FIG. 17 is a view as in FIG. 16 with a filter layer applied to the subframe.

In each embodiment, the wall structure 36 may be made from a substantially rigid material that maintains shape and facilitates its mounting to its respective frame, or be made with a subframe 88, as shown in one exemplary form in FIGS. 16 and 17, that has a more rigid construction that holds shape and lends itself to stable connection to one of the frame configurations. As shown, the subframe 88 has a skeletal shape preformed to the desired end shape for the wall structure 36. Filtration can be carried out by applying one or more layers 90 of suitable construction over the subframe 88 at the front and/or the rear side of the subframe 88. The subframe 88 may be made with a construction that allows reshaping and maintenance of a selected reconfigured shape.

The subframe 88 need not extend fully around the perimeter of the associated cover assembly.

Figure 18:
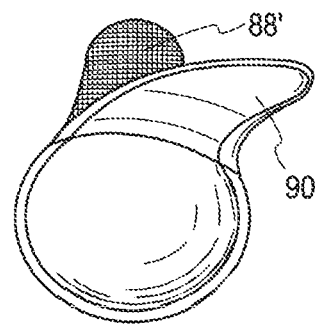
FIG. 18 is a view as in FIGS. 16 and 17 of a modified form of subframe with a filter layer partially peeled away therefrom.

In an alternative construction as shown in FIG. 18, a subframe 88' consists of a formable, preferably metal mesh-type material which has sufficient rigidity to maintain different selected shapes but which at the same time may be conformable enough to allow a complementary shape to each user's face to be selected. As in the prior embodiment, one or more layers 90 can be suitably applied to the front and/or the rear of the subframe 88'.

Figure 19:
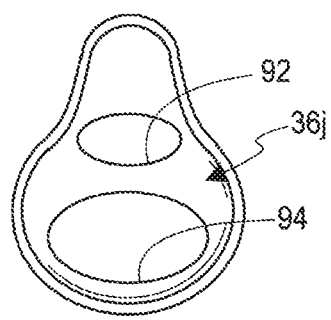
FIG. 19 is a view as in FIGS. 16-18 and showing a further modified form of wall structure as shown in FIG. 3.

In an alternative construction, as shown in FIG. 19, a wall structure 36j has a substantially rigid nonporous shape with strategically located openings 92, 94 formed therein which can be covered by an appropriate filtering material.

Figure 20:
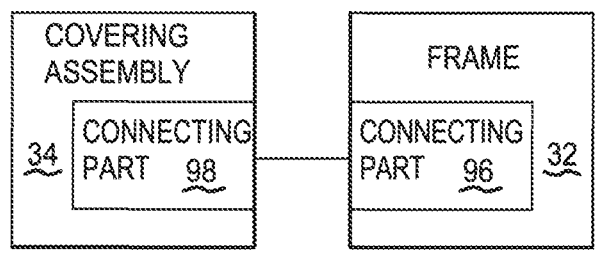
FIG. 20 is a schematic representation of a connection between the frame and covering assembly as shown in FIG. 3.

The connection between the frame 32 and covering assembly 34 is not limited to requiring a subframe. As shown in FIG. 20, the invention contemplates any type of joining of the covering assembly 34 and frame 32 by utilizing any configuration of cooperating connector parts 96, 98, respectively on the frame 32 and covering assembly 34. Slide fit or snap fit connectors may be desirable to allow simple and quick replacement of covering assemblies to change look or to substitute clean or different types of covering assembly 34.

Figure 21:
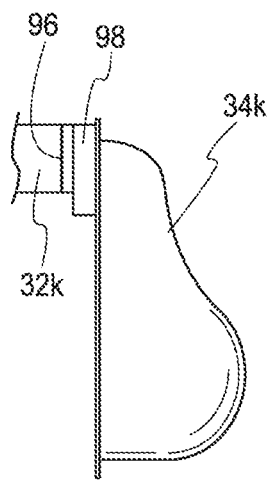
FIG. 21 is a side elevation view of one specific form of connection between a frame and wall structure as shown in FIG. 3.

For example, as shown in FIG. 21, a covering assembly 34k is shown with the connector part 98 separately attached thereto that is suitably joined by the connector part 96 on the frame 32k. The connection may be releasable or permanent, one that fixes the relationship of the frame 32k and covering assembly 34k', or one that allows relative movement therebetween, etc.

The connector 98 may function as part of the aforementioned subframe 56 or may be considered a separate part therefrom.

As noted above, it is also contemplated that one piece may define part of the frame 32 and covering assembly 34 to facilitate stable maintenance of the wall structure 36 on the frame 32.

Figure 22:
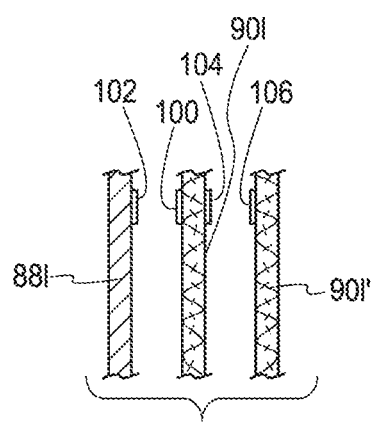
FIG. 22 is a fragmentary, exploded view showing a subframe as in FIG. 16 with multiple filter layers applied thereto.

As shown in FIG. 22, a subframe 88l may use cooperating connectors 100, 102 to maintain a layer 90l against the frame 88l. In turn, cooperating connectors 104, 106 may cooperate to maintain a layer 90l' stacked upon the layer 90l to achieve a cumulative filtering effect.

Figure 23:
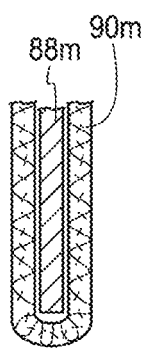
FIG. 23 is a fragmentary, sectional view showing a filter layer connected to a subframe in an alternative manner to that shown in FIG. 22.

In FIG. 23, a filtering layer 90m is wrapped around a subframe 88m to operatively maintain the layer 90m thereon.

Figure 24:
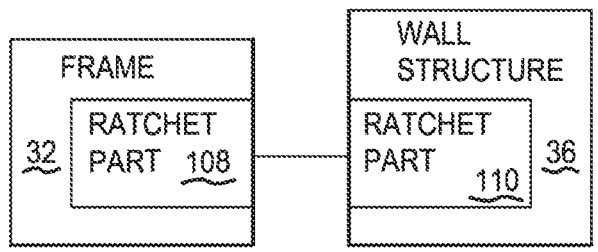
FIG. 24 is a schematic representation of a ratchet connection between a frame and wall structure as shown in FIG. 3.

In FIG. 24, another optional feature is disclosed which allows the wall structure 36 to be repositioned and maintained in different positions relative to the frame 32. As depicted, there are cooperating ratchet parts 108, 110, respectively on the frame 32 and wall structure 36, that permit the wall structure 36 to be moved in stepwise fashion with each of the different positions maintained by the ratchet parts 108, 110. Such an arrangement, while not so limited, is particularly adaptable to the face covering apparatus 30e, 30f in FIGS. 10 and 11, respectively, and may be used to enhance sealing.

Figure 25:
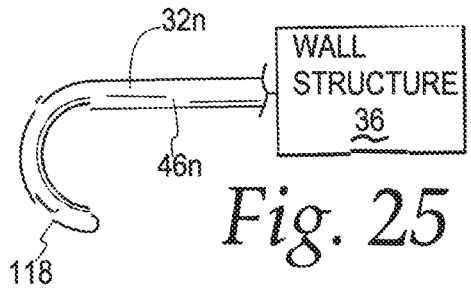
FIG. 25 is a fragmentary, side elevation view of a modified form of arm as usable on frame configurations as in FIGS. 6 and 9.

In FIG. 25, one modification is shown usable with embodiments wherein the frame has legs 46, 48. An exemplary one of the legs 46n may have a turned end 118 which can be wrapped against a wearer's ear and can be configured to positively hold the leg 46n in a rearward position which positively holds the associated frame 32n in place and allows a preloading of the particular wall structure 36 against the wearer's front facial region.

In another variation, as shown in FIG. 6, the aforementioned concept of the subframe 88 may be incorporated, as shown at 88', in the form of discrete subframe components that are strategically placed and have a deformable construction that is shape retentive to allow local shaping of the wall structure 36c for better comfort, conformability, and sealing.

Figure 26:
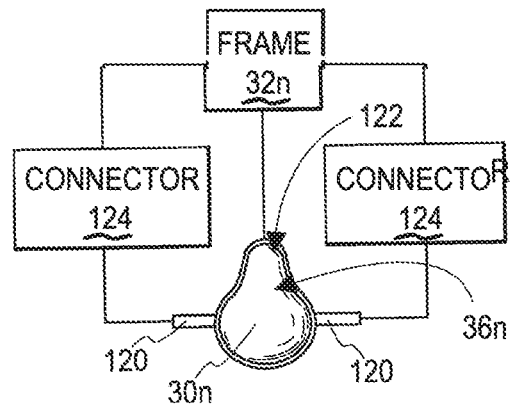
FIG. 26 is a partially schematic, front elevation view of another form of face covering apparatus, as shown in FIG. 3.

In FIG. 26, a further modified face covering apparatus is shown at 30n, consisting of a wall structure 36n with associated adapters 120 which facilitate supplemental reinforcement of the wall structure 36n against the frame 32n. As shown, the wall structure 36n is connected at one location 122 to the frame 32n. Through the adapters 120, one or more connectors 124 can be joined between the adapters and frame 32n at locations spaced from the location 122.

Without limitation, as one example, the connection at the location 122 may be of the type shown in FIG. 10 or 11, with the connectors 124 each in the form of a biasing component, such as one that is elastic, that produces the aforementioned biasing force tending to pivot the wall structure 36n in the direction indicated by the arrow 68 in FIG. 11.

Supplemental rearward biasing of the wall structure 36n, and other wall structures 36 herein, may be achieved by a direct connection between the apparatus 10 and the wearer.

Figure 27:
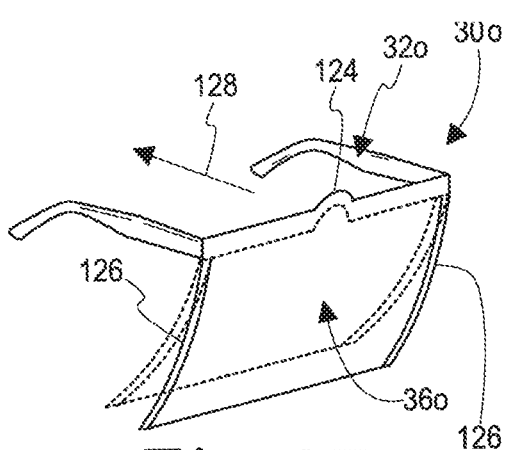
FIG. 27 is a view as in FIGS. 6 and 9 of another form of face covering apparatus as shown in FIG. 3.

As shown at FIG. 27, the face covering apparatus 30o supports a flexible wall structure 36o of the type shown in FIG. 2 made with a sheet or layer that is non-shape retentive and draped against a wearer's face.

The perimeter portion of the wall structure 36o can be attached to the frame 32o, shown with a bridge mount 124 and depending legs 126 which support the wall structure 36o such that it will be drawn conformingly against the wearer's front facial region as the frame 32o is advanced towards its operative position in the direction of the arrow 128.

Figure 28:
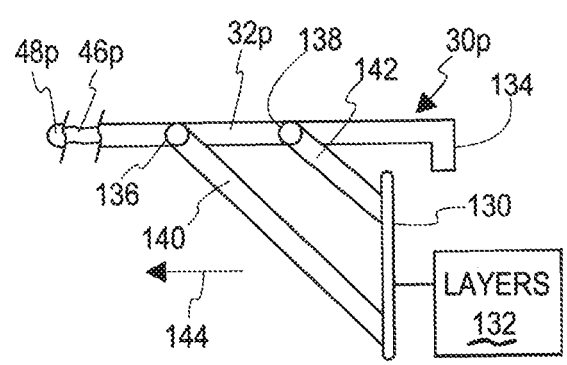
FIG. 28 is a side elevation view of another form of face covering apparatus as shown in FIG. 3.

In an alternative form, as shown in FIG. 28, a subframe 130, consisting of one continuous member or spaced members at opposite sides of the frame, may be used to support one or more layers 132 making up a wall structure as shown in FIGS. 2 and 27. The subframe 130 is mounted on a frame 32p with a temple support 134 and legs 46p, 48p which cooperatively straddle a wearer's head.

Exemplary leg 48p has mounts at locations 136, 138, which respectively support biasing/elastic components 140, 142 extending between respective mount locations 136, 138 and the subframe 130.

As the frame 32p on the face covering assembly 30p is advanced rearwardly towards an operative position, as indicated by the arrow 144, the wearer's face bears against the layers 132 and loads the elastic elements 140, 142 whereby the layers 132 are drawn biasably against a wearer's frontal region to conform thereto.

Figure 29:
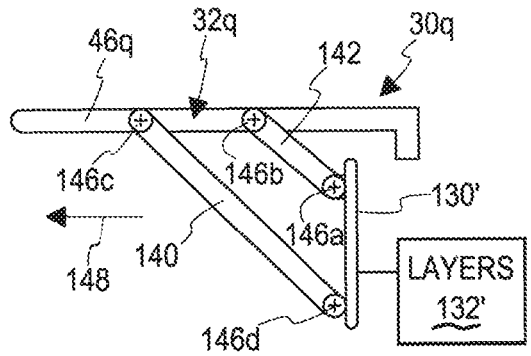
FIG. 29 is a view as in FIG. 28 of yet another form of face covering apparatus as shown in FIG. 3.

In FIG. 29, an apparatus 30q with a similar arrangement as in FIG. 28 is shown wherein a frame 32q uses mechanical linkages 140, 142 at each side, shown in FIG. 28 connecting between the exemplary leg 48q and subframe 130' at one side of the frame 32q. As depicted, the links 140, 142, subframe 130', and leg 48q are connected through spaced pivot connections with axes 146a, 146b, 146c, 146d which allow the layers 132', held in the depending fashion on the subframe 130', to orient over the nose and mouth as the frame 32q on the face covering apparatus 30q is advanced rearwardly in the direction of the arrow 148, causing the supported layers 132' to conform to the wearer's face at the nose and mouth.

The connection at the pivot axes 146 may be unrestrained or there may be a pre-biasing structure incorporated to simulate the function of the FIG. 28 structure, as by using torsion coil springs.

Figure 30:
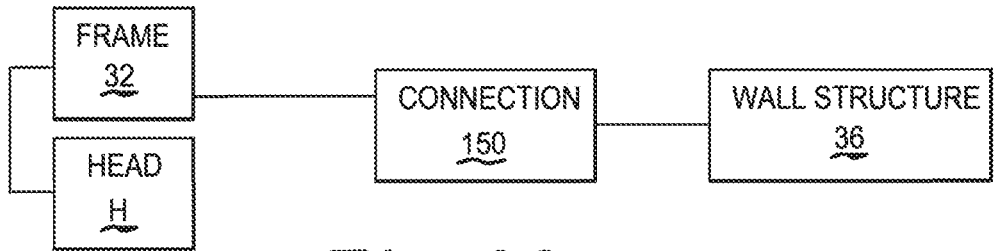
FIG. 30 is a schematic representation of another form of face covering apparatus, according to the present invention.

Generally, as shown in FIG. 30, with each embodiment disclosed, and others contemplated, the frame 32 provides the primary mount for each wall structure 36. By placing the frame 32 in the operative position, the wall structure 36 may be held through an appropriate generically identified connection at 150 in the blocking position on the frame directly in front of the nostrils and mouth of a wearer. As noted above, and in the basic construction, even in a loose, non-sealing arrangement, the wall structure 36 in the blocking position defines a barrier to direct passage of particles horizontally to and from the wearer's nostrils and mouth.

By reason of permitting, but not requiring, the frame 32 to be mounted as described in the specific embodiments described herein, a user may be able to place the frame 32 in an operative position as he/she would place eyewear and headbands—with a single hand. The single movement may finally seat the wall structure 36 or may conveniently support the wall structure 36 for augmented connection to the frame 32 and/or the wearer's head H.

With this basic construction, different versions of face covering apparatus can be developed from a very simple, lightweight structure that provides an unsealed wall structure that blocks horizontal passage of particles to and from the nostril and mouth regions, to a more conformed and sealed arrangement which may be effected as an incident of placing the frame in the operative position or enhanced by further adjustments and use of additional connecting structure. Once the frame is in the operative position, this augmentation of sealing may be made possible by one hand, thereby obviating the need to employ both of the wearer's hands to implement the face covering apparatus. This augmentation may involve manipulation of the apparatus 10 and/or effecting a further connection directly between the apparatus 10 and wearer.

While there is no specific limitation as to the shape and dimensions of a wall structure or with respect to the at least a partially preformed shape as shown in FIG. 5, typically the dimensions will be such as to conform generally to the nose and mouth region as shown for the prior art mask 10 in FIG. 1. This allows the nose to nest within the relatively narrow first region 38, with the region at/above the wearer's chin nesting in the second region 40 without the requirement of significant projection of the wall structure forwardly beyond the wearer's face or significantly above the wearer's nose, which might interfere with a wearer's vision, both in forward and downward directions. The peripheral wall region that engages a wearer's face may be soft and flexible or made more rigid as by selecting an appropriate material, processing a material, and/or by using reinforcement structure, as described above.

With the various embodiments described above, it is possible for the wall structures to be maintained in their blocking positions directly in front of the user's mouth and nostrils without causing discomfort to the wearer. At the same time, the frames can be readily placed in their operative positions and removed therefrom with minimal inconvenience and in most cases by using a single hand. Thus, one has the convenience of picking up the face covering apparatus as he/she would a pair of eyeglasses and placing the frame in an operative position with a simple movement that may not require manipulation of elastic straps and bulky head mountings.

To address the stigma associated with wearing surgical masks in public and to promote healthier habits on an ongoing basis, the face covering apparatus 30 can be made both functional and decorative beyond its basic particle blocking function. In the one embodiment, described above, the wall structure can be integrated into eyeglasses.

To further promote wearing of protective structures, as shown in exemplary FIG. 9, the exposed surface 112 in that embodiment can be adorned with artistic designs or with information in the form of logos, advertising, etc. This information is identified generically in FIG. 9 as "info" at 114 and preferably occupies at least 50% of the exposed area thereof.

This latter construction can be used beneficially at events wherein a large number of attendees are anticipated. For example, at a baseball game, where seats are compactly stacked and people are moving in close proximity to each other in different facing relationships, a face covering apparatus such as that in FIG. 9 could be supplied as a souvenir item. The information 114 may be in the form of a team logo that will inspire people to make a purchase for utility and to have retainable memorabilia.

Even at conferences, as in group meeting rooms, a company's logo may be applied as the "info" to promote teamwork while at the same time addressing health issues.

In a more general sense, in the public, creative adornment on the exposed surfaces may make individuals more comfortable wearing the same consistent with fashion, as opposed to the impression currently conveyed of an individual coping with a dangerous environment.

Figure 31:
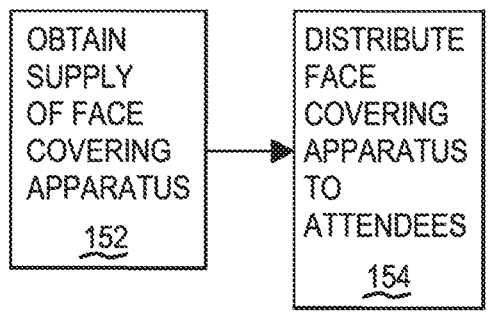
FIG. 31 is a flow diagram representation of a method of equipping attendees at an event to reduce transmission of particles, according to the invention.

With the above-described structure, a method of equipping attendees at an event to reduce oral transmission of particles can be carried out as shown in flow diagram form in FIG. 31.

As shown at block 152, a supply of face covering apparatus, as described above, is obtained, wherein the wall structure has a forwardly facing surface with information pertaining to the event visibly placed thereon.

As shown at block 154, the face covering apparatus are distributed to attendees of the event to be worn during the event.

As noted above, the information may be related to the event and may include a logo associated with a team or an entity sponsoring or participating in the event.

Alternatively, the information may be an advertisement for a product or service, related or unrelated to the event.

The apparatus may be provided gratuitously or sold as a revenue generator.

By providing a generic frame construction with interchangeable wall structures, vendors can keep on hand wall structures/covering assemblies with different appearances. For example, vendors at baseball games can provide wall structures with different team logos as different teams play at that particular venue.

More generally, a manufacturer can offer a generic frame with virtually an unlimited number of differently ornamented wall structures and wall structures that have different information thereon which may be included for entertainment and/or function.

The foregoing disclosure of specific embodiments is intended to be illustrative of the broad concepts comprehended by the invention.

The invention claimed is:

1. A face covering apparatus comprising:
   a frame configured to be placed in an operative position on a wearer's head and releasably maintained in the operative position by at least one of: a) resting upon one or both ears of the wearer and b) frictionally engaging a part of the wearer's head; and
   a covering assembly on the frame and comprising a wall structure with: i) a first region configured to conform to a frontal face region of the wearer around a nose of the wearer; and ii) a second region configured to conform to the wearer's frontal face region around a mouth of the wearer,
   the face covering apparatus configured so that with the frame in the operative position on the wearer's head and the wall structure in a blocking position on the frame, the first and second regions on the wall structure together reside in a path of airborne particles moving: a) in a forward direction from nostrils and/or the mouth of the wearer; and b) in a rearward direction towards the wearer's nostrils and/or mouth,
   wherein the wall structure is movable relative to the frame between the blocking position and a staging position,
   wherein when the frame is in the operative position, at least a part of the wall structure is moved further away from the wearer's frontal face region in the staging position than when the wall structure is in the blocking position,
   wherein the wall structure moves angularly in relationship to the frame through at least 90° between the staging and blocking positions as viewed from a side perspective.

2. The face covering apparatus according to claim 1 wherein the frame is configured to be moved from a position fully spaced from the wearer's head into the operative position by being translated relative to the wearer's head.

3. The face covering apparatus according to claim 2 wherein the frame is configured to be translated along a front to rear line between the position fully spaced from the wearer's head into the operative position.

4. The face covering apparatus according to claim 1 wherein the wall structure has a pre-formed cup shape in which the first and second regions are configured to conform to and overlie at least a part of the wearer's nose and lips of the wearer as viewed from a front perspective.

5. The face covering apparatus according to claim 1 wherein with the frame in the operative position, the first region fully blocks the wearer's nostrils and the second region fully blocks the wearer's mouth as viewed from in front of the wearer.

6. The face covering apparatus according to claim 4 wherein the wall structure is at least partially shape retentive and capable of being re-shaped to more closely conform to the wearer's frontal face region and releasably maintained in a re-shaped configuration.

7. The face covering apparatus according to claim 1 wherein the face covering apparatus further comprises at least one lens on the frame that is placed in front of the eyes of the wearer with the frame in the operative position.

8. The face covering apparatus according to claim 1 wherein the wall structure is configured so that the wearer can inhale and exhale air through at least part of the wall structure.

9. The face covering apparatus according to claim 8 wherein the wall structure is made from a material configured so that the wearer can inhale and exhale air and is configured to trap airborne particles.

10. The face covering apparatus according to claim 1 wherein the second region has a width that is greater than a width of the first region as viewed from a front perspective.

11. The face covering apparatus according to claim 9 wherein the material is a flexible fabric.

12. The face covering apparatus according to claim 11 wherein the covering apparatus has a subframe that maintains a shape of the flexible fabric.

13. The face covering apparatus according to claim 12 wherein the subframe is selectively reconfigurable to thereby allow the flexible fabric to be conformed in at least one of the first and second regions to the frontal face region of the wearer.

14. The face covering apparatus according to claim 1 wherein the frame comprises first and second legs that straddle a part of the wearer's head with the frame in the operative position.

15. The face covering apparatus according to claim 1 wherein the covering assembly is cantilever mounted on the frame.

16. The face covering apparatus according to claim 15 wherein the covering assembly is mounted in depending fashion relative to a part of the frame.

17. A method of equipping attendees at an event to reduce oral transmission of particles, the method comprising steps of:
 obtaining a supply of face covering apparatus as recited in claim 1 wherein the wall structure has a forwardly facing surface and wherein information pertaining to the event is visibly present on the forwardly facing surface; and
 distributing the face covering apparatus to attendees of the event to be worn during the event.

18. The method according to claim 17 wherein the event is a sporting event and the information relates to the sporting event.

19. The method according to claim 18 wherein the information includes a logo associated with a team participating in the event.

20. The method according to claim 17 wherein the information is in the form of an advertisement of a product or service.

21. The method according to claim 17 wherein the face covering apparatus further comprises at least one lens on the frame that is placed in front of the eyes of the wearer with the frame in the operative position.

22. The method according to claim 21 wherein the at least one lens is a prescription lens.

23. The method according to claim 22 wherein the at least one lens is tinted to block the eyes of the wearer from light glare.

24. A method of covering a wearer's face, the method comprising steps of:
 obtaining the face covering apparatus of claim 1; and
 placing the frame in the operative position and thereby causing a part of the wall structure to bear against the wearer's face.

25. The method according to claim 24 wherein the step of placing the frame in the operative position comprises causing a part of the wall structure to conform to the wearer's face.

26. The face covering apparatus according to claim 1 wherein there is a first connector on the frame and a second connector on the covering assembly, the first and second connectors configured to be selectively connected to each other and released from each other, whereby the covering assembly can be selectively connected to and released from the frame.

27. A face covering apparatus comprising:
 a frame configured to be placed in an operative position on a wearer's head and releasably maintained in the operative position by at least one of: a) resting upon one or both ears of the wearer; and b) frictionally engaging a part of the wearer's head,
 the frame having first and second elongate legs extending in front-to-rear lines and configured to reside at opposite sides of the wearer's head with the frame in the operative position; and
 a covering assembly on the frame comprising a wall structure with: i) a first region configured to conform to a frontal face region of the wearer around a nose of the wearer; and ii) a second region configured to conform to the wearer's frontal face region around a mouth of the wearer,
 the face covering apparatus configured so that with the frame in the operative position on the wearer's head and the wall structure in a blocking position on the frame, the first and second regions on the wall structure together reside in a path of airborne particles moving: a) in a forward direction from nostrils and/or the mouth of the wearer; and b) in a rearward direction towards the wearer's nostrils and/or mouth,
 wherein the wall structure is movable relative to the frame between the blocking position and a staging position,
 wherein when the frame is in the operative position, at least a part of the wall structure is moved further away from the wearer's frontal face region in the staging position than when the wall structure is in the blocking position, wherein with the frame in the operative position and the wall structure in the staging position a part of the wall structure is located above the front-to-rear lines of the first and second elongate legs.

28. The face covering apparatus according to claim 27 wherein the face covering apparatus further comprises at least one lens on the frame configured to be placed in front of eyes of the wearer with the frame in the operative position.

29. The face covering apparatus according to claim 28 wherein the at least one lens is tinted to block the eyes of the wearer from light glare.

* * * * *